(12) United States Patent
Beuhler et al.

(10) Patent No.: US 7,091,386 B1
(45) Date of Patent: Aug. 15, 2006

(54) METHOD FOR FACILITATING CATALYZED OXIDATION REACTIONS, DEVICE FOR FACILITATING CATALYZED OXIDATION REACTIONS

(75) Inventors: Robert J. Beuhler, East Moriches, NY (US); Michael G. White, Blue Point, NY (US); Jan Hrbek, Rocky Point, NY (US)

(73) Assignee: U.S. Department of Energy, Washington, DC (US)

( * ) Notice: Subject to any disclaimer, the term of this patent is extended or adjusted under 35 U.S.C. 154(b) by 200 days.

(21) Appl. No.: 10/839,452

(22) Filed: May 3, 2004

(51) Int. Cl.
  *C07C 45/29* (2006.01)
  *C07C 45/35* (2006.01)
  *C07C 45/36* (2006.01)
  *C07D 301/03* (2006.01)
  *C07D 301/10* (2006.01)

(52) U.S. Cl. ............... 568/473; 568/802; 549/523; 549/534

(58) Field of Classification Search ........ 568/473, 568/802; 549/523, 534
See application file for complete search history.

(56) References Cited

U.S. PATENT DOCUMENTS 4,786,743 A * 11/1988 Bongaarts et al. .......... 549/534

OTHER PUBLICATIONS

Beuhler et al. Study of the Partial Oxidation of Methanol to Formaldehyde on a Polycrystalline Ag Foil. Journal of Physical Chemistry B, vol. 105 (25), 2001, p. 5950-5956.*
Jorgensen et al. Oxygen Transfer to Ethylene Catalyzed by the Ag(110) Surface: Possible Adsorption Sites for Molecular and Atomic Oxygen and a Model for the Oxygen Transfer Step. □□Journal of Physical Chemistry, 1990, vol. 94, p. 3046-3054.*
Backx et al. Reactivity of Oxygen Adsorbed on Silver Powder in the Epoxidation of Ethylene.□□Journal of Catalysis, vol. 72 (2), 1981, p. 364-368.*

* cited by examiner

*Primary Examiner*—Sikarl A. Witherspoon
(74) *Attorney, Agent, or Firm*—Joy A. Alwan; Mark P. Dvorscak; Paul A. Gottlieb

(57) ABSTRACT

A catalytic process for the oxidation of organic. Oxygen is loaded into a metal foil by heating the foil while in contact with an oxygen-containing fluid. After cooling the oxygen-activated foil to room temperature, oxygen diffuses through the foil and oxidizes reactants exposed to the other side of the foil.

12 Claims, 7 Drawing Sheets

METHOD FOR FACILITATING CATALYZED OXIDATION REACTIONS, DEVICE FOR FACILITATING CATALYZED OXIDATION REACTIONS

CONTRACTUAL ORIGIN OF INVENTION

The United States Government has rights in this invention pursuant to Contract No. W-31-109-ENG-38 between the U.S. Department of Energy and the University of Chicago, representing Argonne National Laboratory.

BACKGROUND OF THE INVENTION

1. Field of the Invention

The invention relates to an improved process for carrying out oxidation reactions on silver foil at temperatures much lower than typically used, and, more specifically, this invention relates to an improved process for the production of formaldehyde, ethylene oxide, propylene oxide, and phenol at room temperature.

2. Background of the Invention

The reaction of methanol to form formaldehyde is a large-scale industrial process carried out over silver or copper catalysts. The 1997 worldwide production was in excess of $1.5 \times 10^7$ tons. Due to its commercial importance, this reaction has been studied extensively in efforts to improve the efficiency of the process and to understand the reaction on a molecular basis.

Under oxidizing conditions, the reaction proceeds by the dissociative adsorption of methanol onto a catalytic surface to form the methoxy radical. This is followed by the loss of a methyl hydrogen to form formaldehyde and water which desorb from the surface. The overall reaction is highly exothermic ($\Delta H=-156$ kJ/mole) and can be written as in Equation 1:

$$CH_3OH + O \rightarrow CH_2O + H_2O \qquad \text{Eq. 1}$$

On Ag surfaces, the methanol-to-formaldehyde reaction is optimally run, in commercial operations, at temperatures between 800° K. to 900° K. The $O_2$ molecules undergo dissociative adsorption, with the resulting high mobility oxygen atoms readily dissolving into the Ag bulk.

Previous efforts disclose the use of membranes to effect chemical reactions. U.S. Pat. No. 6,048,472 awarded to Nataraj, et al. on Apr. 11, 2000 discloses a process for the production of synthesis gas by permeating oxygen gas from one side of a mixed conducting membrane through to the other side where reaction occurs.

U.S. Pat. No. 5,430,210 awarded to Grasselli, et al. on Mar. 3, 1995 discloses a process for contacting, at reactive conditions, a hydrocarbon/hydrogen reactant feed stream with one side of a membrane and contacting the other side of the membrane with an oxygen stream.

U.S. Pat. No. 3,375,288 awarded to de Rosset, et al. on Mar. 26, 1968 discloses a process for withdrawing hydrogen from a product liquor so as to enhance yields in dehydrogenation reactions. The '288 patent maintains an oxygen-containing gas on one side of a silver membrane under pressure sufficient to cause oxygen to diffuse through the membrane. This oxygen supply is then utilized to combine with hydrogen to create water.

None of the aforementioned patents anticipate or suggest utilizing activated metal surfaces as a catalytic-type reaction site for oxygenation reactions. Rather, the prior art appears to be relegated to using membranes merely to separate reactant feeds from each other prior to reaction of one or several of the moieties in the feedstock streams.

A need exists in the art for a method for carrying out oxidation reactions at room temperatures. The method should utilize standard metal substrates and be conducted at pressures and temperatures lower than present commercial operations in order to cut operating costs. The method should keep pressurized reactant streams separate from each other to prevent explosions.

SUMMARY OF INVENTION

It is an object of the present invention to provide a method for facilitating oxidation reactions on catalyzed surfaces that overcomes many of the disadvantages of the prior art.

Another object of the present invention is to provide a better method for the commercial oxidation of methanol to formaldehyde. A feature of the invention is that it can be carried out at room temperatures compared to the present commercial temperature of 800° K. An advantage of this invention is that it has lesser costs and is less hazardous.

Still another object of the present invention is to provide a process for carrying out oxidation reactions on the surfaces of activated silver foil at room temperature. A feature of the invention is loading atomic oxygen into one side of silver foil so as to facilitate the sequestration of atomic oxygen on the opposite side of the silver foil. Another feature is that the atomic oxygen oxidizes reactants contacting the opposite side of the silver foil, with the resulting product immediately desorbing from the foil. An advantage of the invention is that the immediate desorption of the oxidized moiety prevents further reaction of the target product molecule.

Yet another object of the present invention is to provide a more efficient and rapid method of activation of the metal foil. A feature of the invention is the use of a pretreated or activated foil having crystalline properties to facilitate rapid oxidation of unsaturated moieties, such as the oxidation of ethylene to ethylene oxide. An advantage of this invention is that the activated foil can remain activated indefinitely for oxidation reactions at the foil surface because oxygen atoms remain dissolved in the silver foil.

Another object of the present invention is to provide oxidation reactions whereby contact between pressurized oxygen and the moiety to be oxidized is minimized. A feature of the invention is the juxtaposition of an oxygen atom permeable foil intermediate to the pressurized reactants. An advantage of this juxtaposition is that it isolates pressurized oxygenated fluids from target moieties, thereby reducing the likelihood of an explosion.

Still another object of the present invention is to lower operating costs in formaldehyde-, ethylene oxide-, propylene oxide-, and phenol-producing processes. A feature of this invention is that the reactions can be carried out at lower temperatures such as room temperature. An advantage of this invention is that it requires less energy and is less expensive.

Briefly, the invention provides a process for the oxidation of a reactant moiety to a product moiety, the process comprising providing a substrate capable of absorbing atoms and desorbing oxygen molecules, and reacting the oxygen atoms on the surface of the substrate; heating the substrate and contacting the heated substrate with molecular oxygen to a time and at a pressure sufficient to cause the substrate to absorb the atomic oxygen; cooling the substrate; and contacting the reactant to the cooled substrate.

In addition, the invention provides a catalytic process for the oxidation of a reactant moiety to a product moiety, the process comprising providing a metal foil capable of absorbing oxygen atoms and delivering the oxygen atoms to a reactive surface; heating the metal foil and contacting the heated metal foil with molecular oxygen to a time and at a pressure sufficient to cause the metal foil to absorb the atomic oxygen; cooling the metal foil; and contacting the reactant to the cooled metal foil.

Finally, the invention provides a device for oxidizing reactant moieties, the device comprising an oxygen atom-permeable substrate; means for heating the substrate; a means for contacting a first surface of the heated substrate with molecular oxygen; a means for allowing the substrate to cool; and a means for contacting a second side of the cooled substrate with the reactant moieties.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
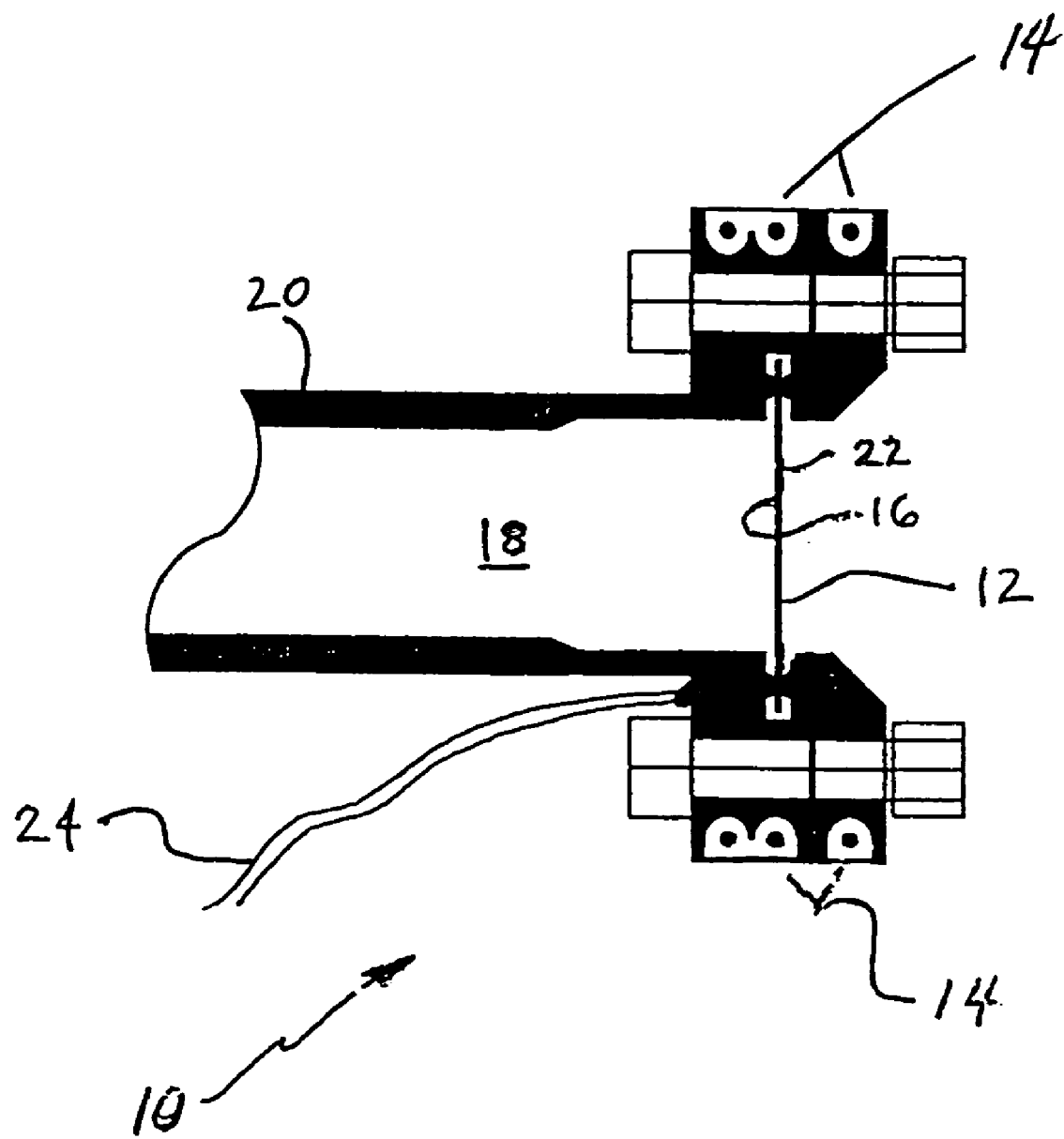
FIG. 1 is a schematic diagram of a device for facilitating oxidation reactions using metal foil, in accordance with features of the present invention.

The invention provides a catalytic process to facilitate oxidation reactions on metal foils at temperatures lower than those typically required in present commercial operations and with greater efficiency. Salient features of the invention are disclosed in R. J. Beuhler et al. *J. Phys. Chem. B*, 105, 5950–5956 (2001), and incorporated herein by reference.

The invented method exploits the phenomenon whereby surface oxygen species are formed on a high vacuum side of a metal foil by diffusion of oxygen atoms through the foil, the atoms generated by dissociative adsorption on the opposite side (i.e., high pressure side). The source of the atoms is oxygen molecules in an oxygen-containing fluid contacting the high pressure side of the metal foil.

The invented method comprises first saturating an oxygen atom-permeable-substrate (silver) on the substrate's high pressure side (contacted with the oxygen containing fluid) with oxygen atoms, then utilizing the saturated substrate as a feedstock of oxygen atoms for oxidation reactions on the substrate's low pressure (vacuum) side.

Active oxygen sites are continuously created on the restructured metal substrate via dissociative adsorption of molecular oxygen from the feed gas. This allows for the most effective use of the invented method in that moieties formed on the reactive side of the foil immediately desorb from the surface, thereby preventing any further reaction with the newly formed moieties. In essence, the oxygen atoms are sequestered to the vacuum or low pressure surface of the foil. When moieties such as methanol, ethylene, propylene, and benzene are contacted to the sequestered atoms, formaldehyde, ethylene oxide, propylene oxide, and phenol respectively, form and immediately desorb from the foil.

The inventors found that high pressure exposure of the foil to an oxygen-containing fluid leads to at least three substrate-bound O atom species with desorption temperatures of 480° K., 600° K. and >900° K. The latter two oxygen species are thought to be bulk dissolved O atoms and strongly bound near-surface O atoms, respectively, whereas the species at 480° K. is believed to both chemisorbed O atoms and molecular oxygen.

Desorption of oxygen molecules stops below about 400° K. Below this temperature, all of the oxygen dissolved in the foil is available for reaction. The oxygen atoms can diffuse through the metal foil at temperatures as low as 300° K. The oxygen comes through as atoms, and these atoms can then react with reactant moiety molecules on the surface.

Metals such as silver have a very high loading capacity for oxygen. Coupled with atomic oxygen's high diffusivity in metal, the high loading capacity allows for using an oxygen-loaded metal membrane without additional gaseous molecular oxygen on the oxygen-loading side of the membrane. Removal of oxygen-containing fluid from the oxygen side of the metal foil, after the foil has been fully loaded with oxygen, does not drastically reduce the rate of product formation simply because there is so much atomic oxygen dissolved in the metal.

Surprisingly and unexpectedly, the inventor has found that pretreating the foil prior to using same for the oxygenation process increases the reactivity of the silver foil in the oxidation reaction. Specifically, this pretreatment protocol comprises recrystallizing the surface of the metal substrate by exposing the foil to oxygen for a time and at a temperature sufficient to impart morphology changes to the bulk of the foil with facet formation at the surface of the substrate having low index faces.

A longitudinal cutaway of an exemplary device for preparing the oxygen-saturated substrate is depicted in FIG. 1 as numeral 10. A metal foil 12 is in thermal communication with a means 14 for heating the foil. In the device shown, the heating means contacts the periphery of the foil so as to effect heat transfer to the foil via thermal conductance. A thermocouple 24 monitors the heating means 14.

A first surface 16 of the foil 12 is in fluid communication with a passageway 18 formed by a conduit 20, one end of which terminates at the first surface 16.

A second surface 22 of the foil faces in a direction opposite the first surface 16. The second surface is substantially hermetically sealed from the passageway 18.

In operation, metal foil is heated to a temperature between 300 and 1000 degrees Kelvin (° K.). The first surface is then contacted with an oxygen-containing fluid. Oxygen molecules from the fluid then undergo dissociative adsorption inasmuch as O atoms have high mobility and readily dissolve into the metal bulk. The foil is then considered to be loaded with oxygen atoms. The shelf-life of this oxygen-atom loaded substrate is indefinite, so long as the activated substrate is not exposed to moieties which can readily undergo oxidation.

After activation, the foil is cooled to between 300° K. and 400° K. The oxygen atoms then diffuse to the second surface 22 of the metal, which is in contact with an alcohol. The alcohol can be supplied at a pressure of approximately $1\times10^{-1}$ to $1\times10^{10}$ Torr.

Figure 2:
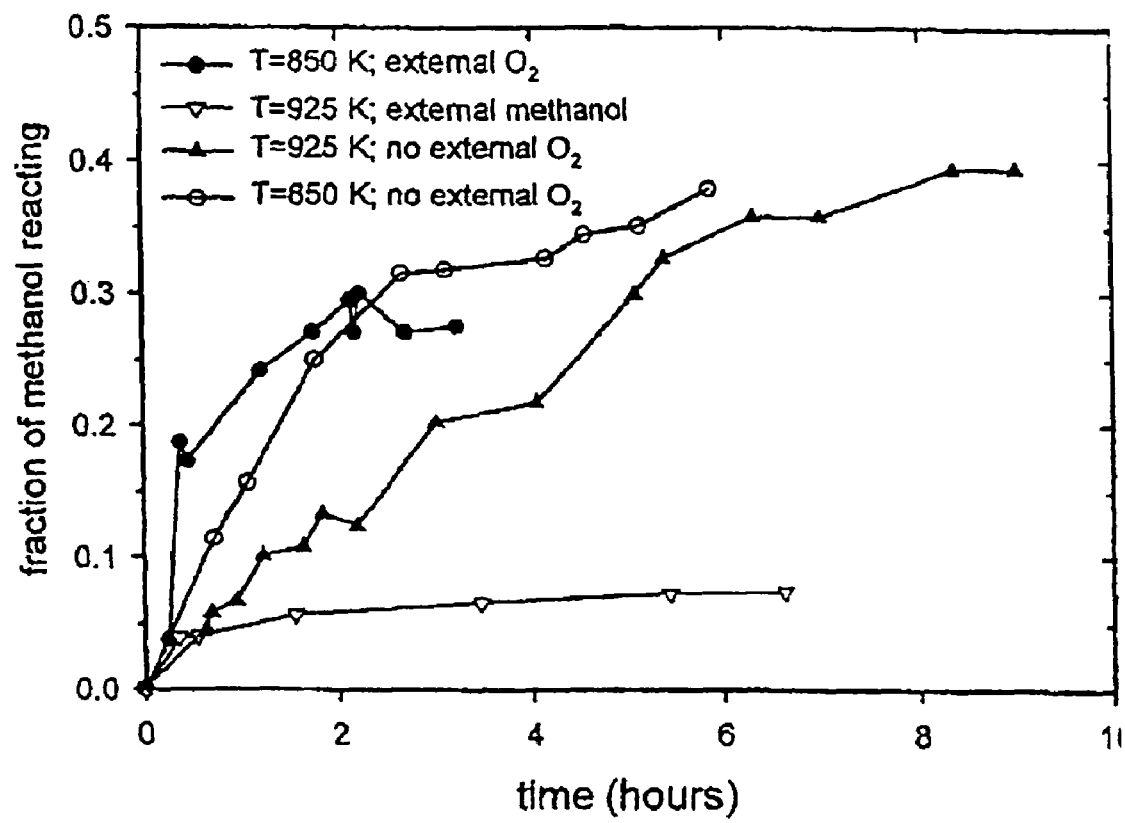
FIG. 2 is a graph of the fraction of methanol reacting as a function of time and at different temperatures, in accordance with features of the present invention.

The activation of the foil's surface causes the reaction to proceed with higher efficiency. FIG. 2 is a plot of the fraction of methanol reacting as a function of time at different temperatures. As can be seen, very little reactivity exists in the first hour of heating. The curve for the temperature of 850° K. peaks more quickly at its maximum than the curves for the other temperatures. The slope of the curve for the data taken at 850° K. is much steeper than the curve for the similar data taken at 950° K. This demonstrates 850° K. to be a best temperature of activation. As noted supra, the activation process is speeded up if the foil surface on which the reaction is to take place is itself activated by being pretreated with oxygen.

Figure 3:
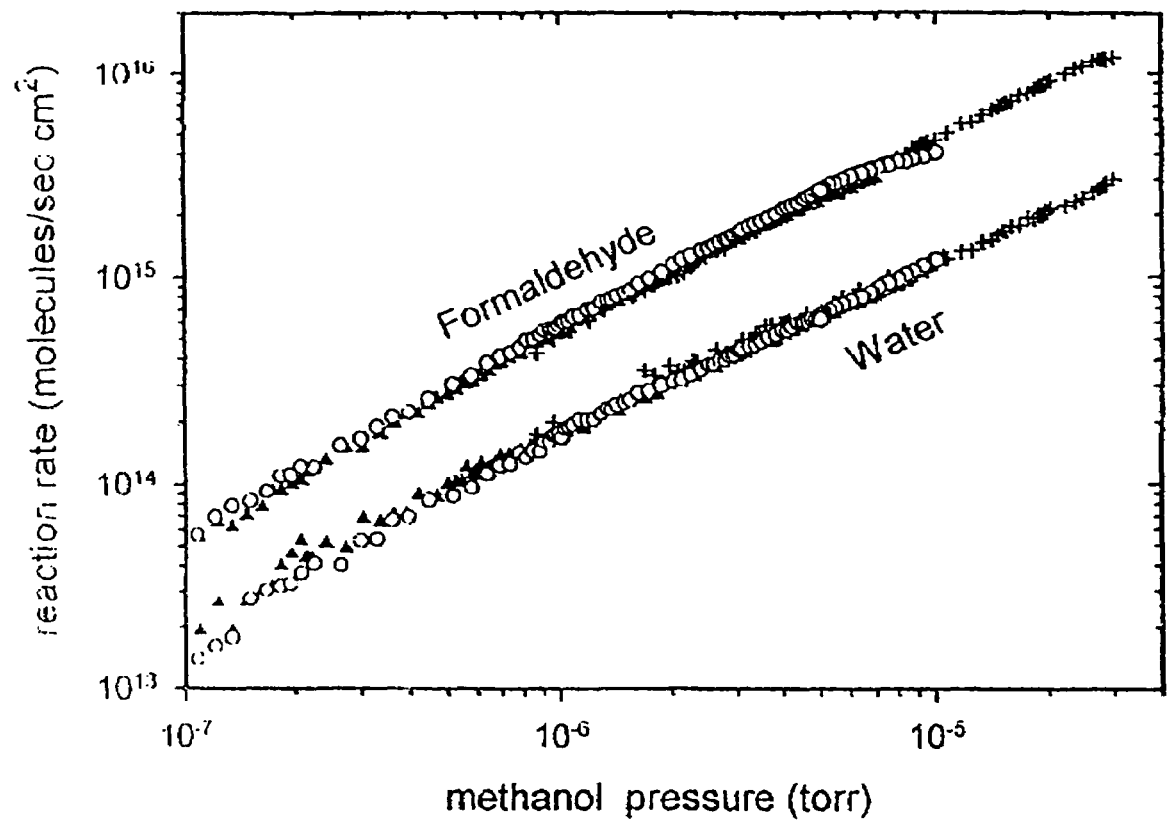
FIG. 3 is a schematic diagram of the pressure dependence of the reaction rate for the formation of formaldehyde and water on an activated silver foil at 877 K, in accordance with features of the present invention.

FIG. 3 displays pressure dependence of the reaction rate for the formation of formaldehyde and water on an activated silver foil at 877° K. The reaction rates for both formaldehyde and water formation exhibit a near linear dependence on the methanol pressure, with the water showing a slight change in slope as the methanol pressure is increased above $10^{-6}$ Torr. For formaldehyde, the slope of the rate curve is close to one. At those low pressures, the rates of formaldehyde and water formation are first-order in methanol pressure, that is, the rates have a linear dependence upon the methanol pressure, and its concentration.

The inventors found that removal of oxygen from the molecular oxygen side (first surface 16) of the metal foil, after the foil has been fully loaded with oxygen, does not drastically reduce the rate of formaldehyde formation. This is most likely due to the great capacity of the metal foil to "load", with molecular and atomic oxygen. The ratio of oxygen atoms to metal atoms in a "loaded" foil can approach one to one.

Optimum temperatures for the process are between 300° K. to 1000° K. with temperatures in the general vicinity of room temperature being preferred. Room-temperature reactivity is maintained for long periods of time without a significant drop in the formation rates.

FIG. 4a displays formaldehyde formation rates in molecules/s-cm² as a function of temperature on activated Ag membrane. The rate of formaldehyde formation is approximately $1\times10^{14}$ to $7\times10^{14}$ molecules/s-cm², when the metal foil is Ag foil. The rate of formaldehyde formation decreases by less than a factor of two as the temperature is decreased from 900° K. to room temperature (293° K.).

FIG. 4b displays two similar reaction patterns for the fraction of methanol reacting as a function of temperature, also on activated Ag membrane.

Figure 5:
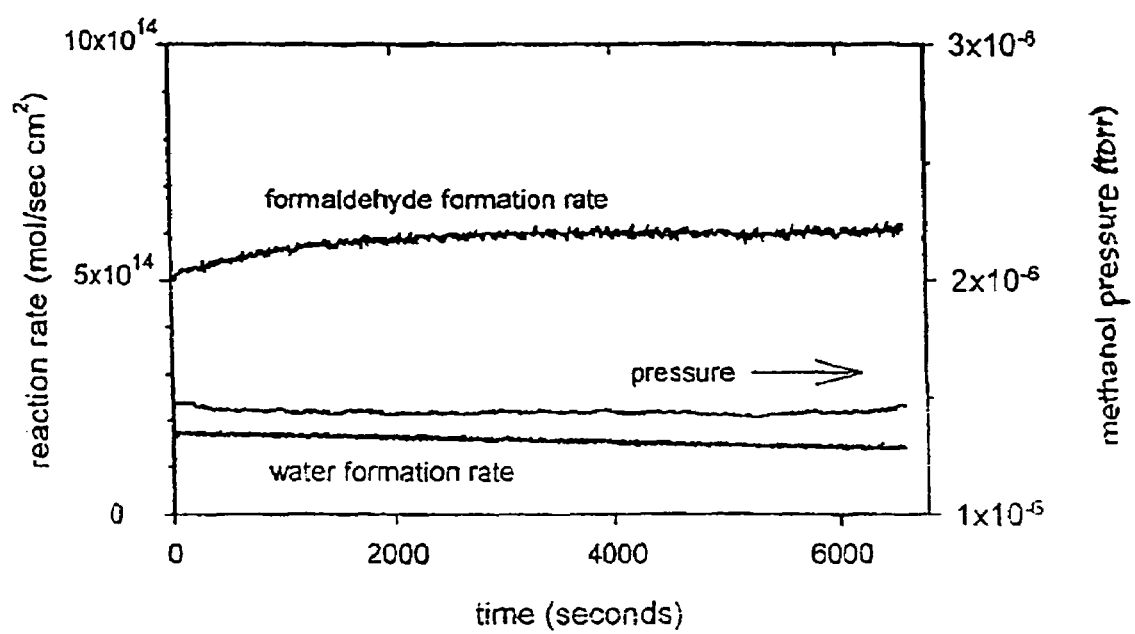
FIG. 5 is a graph of the rate of formation of formaldehyde from a room-temperature silver foil as a function of exposure time to methanol, in accordance with features of the present invention.

FIG. 5 displays the rate of formaldehyde formation from a room-temperature silver foil as a function of exposure time to methanol wherein the methanol pressure was $1\times10^{-6}$ Torr. The formation rates show very little change over the entire exposure time of 7000 seconds and the formaldehyde formation rate actually shows a slight increase with time, which suggests that O atoms dissolved in the metal bulk can rapidly diffuse to active surface sites. The line just below the word "pressure" is the methanol pressure as a function of time.

While a myriad of temperature exposure times can be utilized, i.e., from 0.25 hours to 5 hours, the highest reaction rates are obtained after approximately 0.5 to 1.5 hours of high temperature exposure and 0.5 to 1.5 hours of high oxygen exposure.

A myriad of oxygen-containing fluids are suitable feedstocks for the process. Preferably, the oxygen containing fluid is selected from the group consisting of air, oxygen gas, ozone, an oxygen containing molecule in an electrical discharge, or a combination thereof.

Oxygen-containing fluid pressure during the heating and cooling phases is between 200 and 1500 torr. The thickness of the metal foil is between 0.10 millimeter (mm) to 1.0 millimeter. Loading of oxygen from the oxygen-containing fluid into the foil can be as much as $5.6\times10^{21}$ atoms of oxygen per gram of metal.

Formation of ethylene oxide from ethylene, propylene oxide from propylene, and phenol from benzene would most likely display similar kinetics characteristics as does the methanol-formaldehyde system. The rate of formation of ethylene oxide, propylene oxide, and phenol would probably be first-order in terms of their respective reactant moieties' (ethylene, propylene, and benzene) pressures at low pressures. Characteristics of the activated silver foil would remain the same.

Substrate/Reactant

Detail

The reactant moiety comes from the group consisting of alcohols, aldehydes, and hydrocarbons, both aliphatic and aromatic. Each alcohol comes from the group consisting of methanol, ethanol, n-propanol, isopropanol, n-butanol, and isobutanol.

The product moiety produced by the partial oxidation of alcohols comes from the group consisting of formaldehyde, acetaldehyde, propionaldehyde, acetone, butyraldehyde, and ethyl methyl ketone. The product moiety produced by full oxidation of alcohols comes from the group consisting of formic acid, acetic acid, propionic acid, and butyric acid.

Exemplary aldehydes come from the group consisting of formaldehyde, acetaldehyde, propionaldehyde, and butyraldehyde. Each product moiety produced by oxidation of an aldehyde comes from the group consisting of formic acid, acetic acid, propionic acid, and butyric acid.

Exemplary aliphatic hydrocarbons come from the group consisting of methane, ethane, propane, butane, ethylene, and propylene.

Exemplary product moieties produced by partial or full oxidation of an aliphatic hydrocarbon comes from the group consisting of formaldehyde, formic acid, acetaldehyde, acetic acid, propionaldehyde, propionic acid, butyraldehdye, butyric acid, ethylene oxide, and propylene oxide.

Exemplary aromatic hydrocarbons come from the group consisting of benzene and naphthalene.

Each product moiety produced by partial or full oxidation of an aromatic hydrocarbon comes from the group consisting of phenol and naphthol.

The following example is for illustrative purposes only. As such, other reactants, and therefore their respective oxidized products are candidates for use in the invented device and method.

EXAMPLE

Silver foil was cleaned and polished on both sides with polishing agent such as alumina. Subsequent to an overnight bake under high vacuum (~$10^{-9}$ Torr), each new foil was heated to temperatures greater than 800° K. with 400 Torr of oxygen on the high-pressure side for several hours. Commercially available oxygen gas was used without further purification. The reactivity of the Ag-membrane at high temperatures was periodically checked by introducing methanol at a pressure of about $5\times10^{-6}$ Torr and extracting the reacting fraction of methanol. Analytical reagent grade methanol was utilized and degassed via repeated freeze-thaw cycles.

The inventors have found that for a methanol pressure of $1\times10^{-6}$ Torr, the maximum rate of formaldehyde formation is $7\times10^{14}$ mol/s-cm$^2$ at 900° K. and only decreases by a factor of two as the foil temperature is reduced to 300° K. Reaction at room temperature is attributed to the high diffusion rate of O atoms dissolved in the bulk which maintains the surface oxygen concentration sufficiently high to achieve reaction rates of $5\times10^{14}$ mol/s-cm$^2$ for hours when the methanol pressure is held at $2\times10^{-6}$ Torr.

Figure 4:
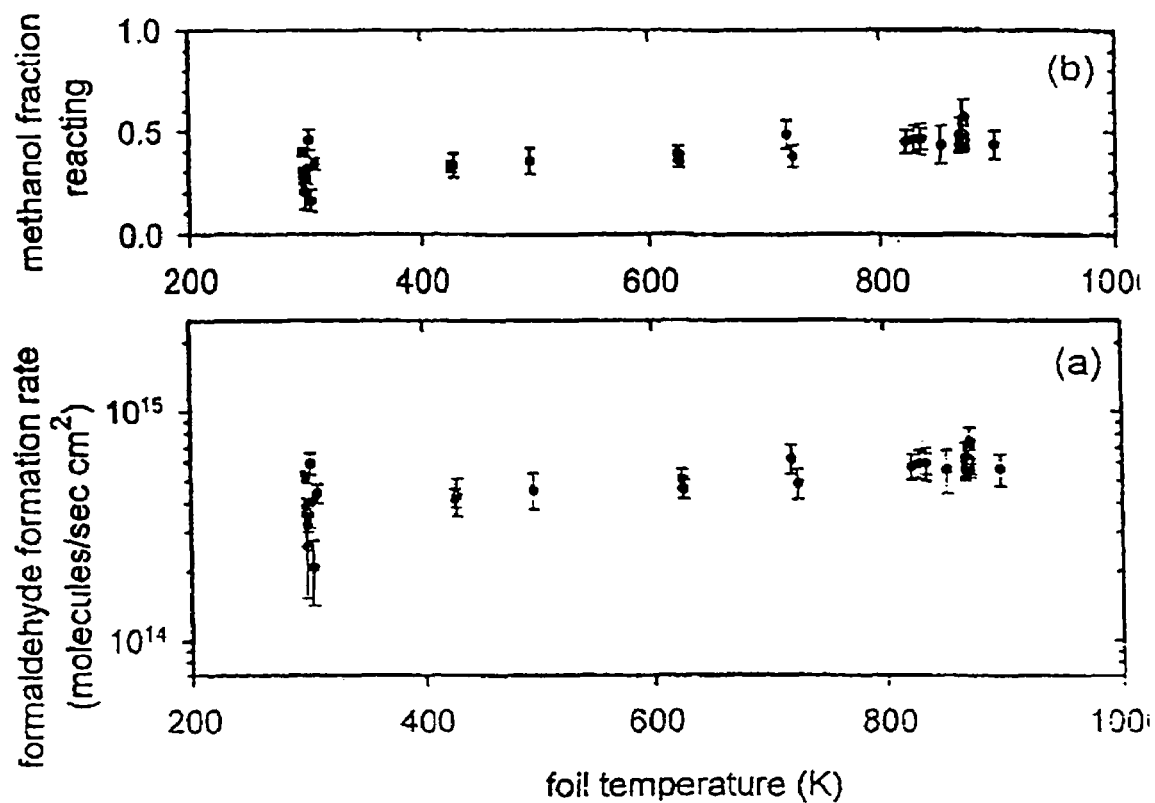
FIGS. 4(*a–b*) are graphs of formaldehyde formation rates as a function of temperature on activated Ag membrane, in accordance with features of the present invention.

The rate data in FIG. 4 were obtained with 400 Torr of oxygen behind the Ag foil, which at 877° K. results in permeation of O atoms through the foil to the surface where they can recombine and desorb as molecular oxygen. Under these conditions, the desorbing $O_2$ partial pressure was $\sim 8\times10^{-8}$ Torr. Once the Ag foil is saturated with oxygen atoms, removing oxygen from behind the foil has very little effect on the rate of formaldehyde formation even though the flow of O atoms into the foil is stopped as measured by the partial pressure of $O_2$.

Figure 6:
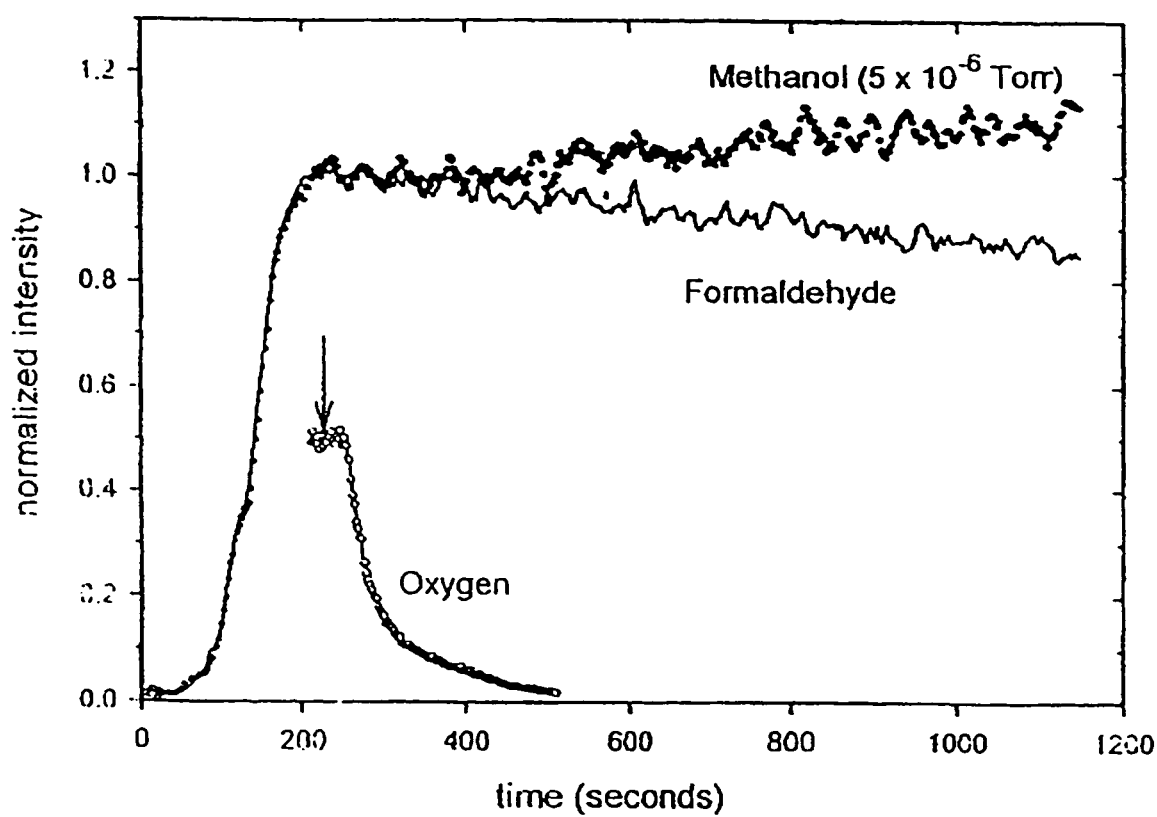
FIG. 6 is a graph depicting formaldehyde formation in the presence, and then the absence, of oxygen on the high pressure side of the foil.

FIG. 6 displays the effect on the formaldehyde yield of evacuating the $O_2$ from the high pressure side of an activated Ag foil. The arrow indicates the time at which the oxygen behind the silver membrane was evacuated, which has little effect on the formaldehyde product yield (solid line). The yield of desorbed oxygen molecules (open circles) after $O_2$ evacuation was measured in a separate experiment with no methanol present. This phenomenon of continued foil activity to form oxidized products is attributed to the very high oxygen loading of the activated Ag-foil and the high diffusivity of dissolved oxygen.

Figure 7:
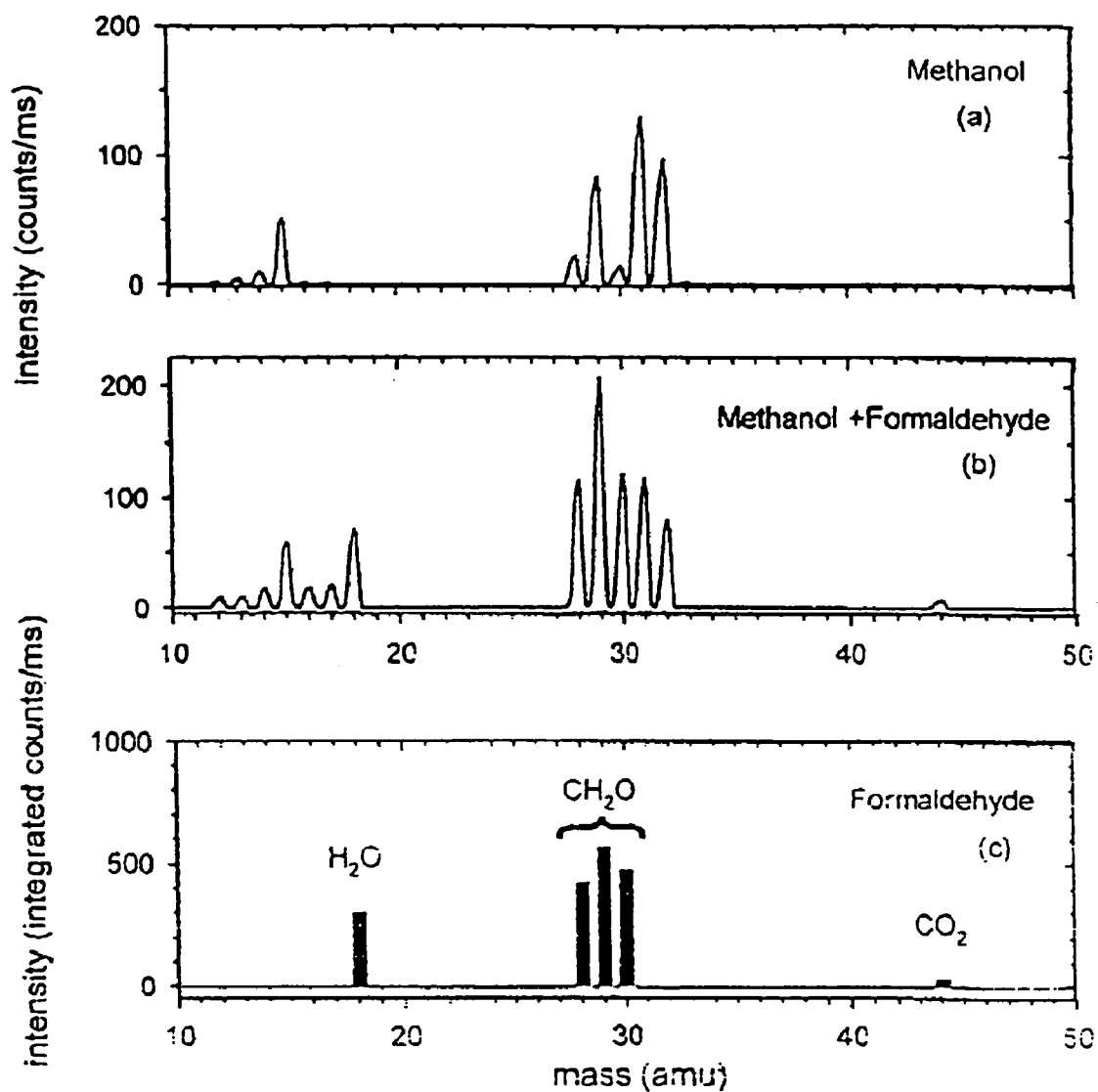
FIGS. 7 (*a–c*) are mass spectra of reactant methanol and its oxidation product, formaldehyde, produced in accordance with features of the present invention.

FIGS. 7(a–b) display schematic diagrams of mass spectra for which back-ground mass spectra, taken when no methanol is present, have been subtracted from both spectra. FIG. 7a is a mass spectrum of methanol without any oxidation reaction and was obtained by exposing methanol to a new Ag foil prior to heating and activation by oxygen permeation. The observed fragmentation pattern is characteristic of methanol. Under conditions where the Ag foil is activated and methanol is placed on the activated surface (FIG. 7b), the mass peaks at 28–30 atomic mass units (amu) are significantly enhanced, and the 29/30 ($HCO^+/CH_2O^+$) fragment ion intensity ratio is reduced from 6.6 to 1.7. These changes reflect a high yield of formaldehyde product and the characteristic fragment ion spectrum of formaldehyde as seen in the difference spectrum given in FIG. 7c. The other reaction product, water (18 amu), is evident and there is a trace of $CO_2$ (44 amu). Other products such as formic acid or methyl formate, with parent ions at mass 46 and mass 60, respectively, could not be distinguished above the background and thereby contribute less than 0.1% to the ion intensity at mass 29.

While the invention has been described with reference to details of the illustrated embodiment, these details are not intended to limit the scope of the invention as defined in the appended claims.

The invention claimed is:

1. A catalytic process for the oxidation of a reactant moiety to a product moiety, the process comprising:
   a) providing a silver foil substrate having a first surface and a second surface opposite the first surface capable of absorbing oxygen atoms and desorbing oxygen molecules;
   b) heating the substrate and contacting the first surface of the heated substrate with molecular oxygen for approximately 0.5 to 1.5 hours and at a pressure sufficient to cause the substrate to absorb the atomic oxygen;
   c) cooling the substrate to a temperature between 300 and 400 degrees Kelvin;
   d) contacting the first surface of the foil to a high pressure oxygen containing fluid;
   e) applying a vacuum to the second surface of the foil; and
   f) contacting the second surface of the foil with a reactant selected from the group consisting of methanol, ethylene, propylene, benzene or combinations thereof, thereby oxygenating the reactant.

2. The process as recited in claim 1 wherein the substrate is heated to a temperature between 300 and 1000 degrees Kelvin.

3. The process as recited in claim 1 wherein the molecular oxygen is applied at a pressure of between 200 and 1500 torr.

4. The process as recited in claim 3 wherein the oxygen is in contact with the substrate for a time sufficient to load the substrate with between $10^{18}$ and $10^{21}$ atoms of oxygen per gram of metal.

5. The process as recited in claim 1 wherein the thickness of the substrate is between 0.05 millimeter (mm) to 1.0 millimeter (mm).

6. The process as recited in claim 1 wherein the process occurs at between 300 to 1000 degrees Kelvin.

7. A catalytic process for the oxidation of a reactant moiety to a product moiety, the process comprising
   a) providing a metal foil capable of absorbing oxygen atoms and delivering the oxygen atoms to a surface of the foil;
   b) heating the metal foil and contacting the heated metal foil with molecular oxygen to a time and at a pressure sufficient to cause the metal foil to absorb atomic oxygen;
   c) cooling the metal foil to a temperature between 300° and 400° K.; and,
   d) contacting the reactant to the cooled metal foil.

8. The process as recited in claim 7 wherein the metal is silver.

9. The process as recited in claim 7 wherein the foil is heated to a temperature between 300 and 1000 degrees Kelvin.

10. The process as recited in claim 7 wherein the oxygen is in contact with the metal foil for a time sufficient to load the substrate with between $10^{18}$ and $5.6\times10^{21}$ atoms per gram of metal.

11. The process as recited in claim 7 wherein the process occurs at between 300 to 1000 degrees Kelvin.

12. The process as recited in claim 7 wherein the reactant is selected from the group consisting of methanol, ethylene, propylene, benzene, or combinations thereof.

* * * * *